US 6,741,892 B1

(12) United States Patent
Meadows et al.

(10) Patent No.: US 6,741,892 B1
(45) Date of Patent: May 25, 2004

(54) MOVABLE CONTACT LOCKING MECHANISM FOR SPINAL CORD STIMULATOR LEAD CONNECTOR

(75) Inventors: Paul M. Meadows, La Crescenta, CA (US); Larry D. Devor, Menifee, CA (US); Stephen L. Goldman, Stevenson Ranch, CA (US)

(73) Assignee: Advanced Bionics Corporation, Sylmar, CA (US)

( * ) Notice: Subject to any disclaimer, the term of this patent is extended or adjusted under 35 U.S.C. 154(b) by 493 days.

(21) Appl. No.: 09/799,214

(22) Filed: Mar. 5, 2001

Related U.S. Application Data

(60) Provisional application No. 60/188,967, filed on Mar. 10, 2000.

(51) Int. Cl.$^7$ .................................................. A61N 1/375
(52) U.S. Cl. ........................... 607/116; 607/37; 607/46; 607/117
(58) Field of Search .................. 607/116, 30, 118, 607/37, 38, 36, 43, 46, 117; 606/129

(56) References Cited

U.S. PATENT DOCUMENTS

| | | | | |
|---|---|---|---|---|
| 4,142,532 A | 3/1979 | Ware | ............................ | 128/419 |
| 4,180,078 A | 12/1979 | Anderson | .................... | 128/419 |
| RE31,990 E | 9/1985 | Sluetz et al. | ................. | 128/419 |
| 4,540,236 A | 9/1985 | Peers-Trevarton | ............ | 339/45 |
| 4,840,580 A | 6/1989 | Saell et al. | .................. | 439/431 |
| 4,850,359 A | 7/1989 | Putz | ............................ | 128/642 |
| 4,860,750 A | 8/1989 | Frey et al. | ................... | 128/419 |
| 4,869,255 A | 9/1989 | Putz | ............................ | 128/642 |
| 5,070,605 A | 12/1991 | Daglow et al. | ................ | 29/842 |
| 5,082,453 A | 1/1992 | Stutz, Jr. | ..................... | 439/265 |
| 5,241,957 A | 9/1993 | Camps et al. | ................. | 607/119 |
| 5,354,326 A | 10/1994 | Comben et al. | ............. | 607/115 |
| 5,358,514 A * | 10/1994 | Schulman et al. | ........... | 607/118 |
| 5,560,358 A | 10/1996 | Arnold et al. | ............... | 128/642 |
| 5,766,042 A | 6/1998 | Ries et al. | .................... | 439/668 |
| 5,782,892 A | 7/1998 | Castle et al. | .................... | 607/37 |
| 5,800,495 A * | 9/1998 | Machek et al. | ............... | 607/116 |
| 5,843,141 A | 12/1998 | Bischoff et al. | ............... | 607/37 |
| 5,906,634 A | 5/1999 | Flynn et al. | ................... | 607/37 |
| 5,968,082 A | 10/1999 | Heil | ............................ | 607/37 |
| 5,989,077 A | 11/1999 | Mast et al. | ................... | 439/814 |
| 6,006,135 A | 12/1999 | Kast et al. | ..................... | 607/37 |
| 6,038,479 A | 3/2000 | Verner et al. | ............... | 607/115 |
| 6,038,481 A | 3/2000 | Verner et al. | ............... | 607/119 |
| 6,112,120 A * | 8/2000 | Correas | ........................ | 607/37 |
| 6,112,121 A | 8/2000 | Paul et al. | ..................... | 607/37 |
| 6,154,678 A | 11/2000 | Lauro | .......................... | 607/115 |
| 6,198,969 B1 * | 3/2001 | Kuzma | .......................... | 607/37 |
| 6,321,126 B1 * | 11/2001 | Kuzma | .......................... | 607/38 |
| 6,587,724 B2 * | 7/2003 | Mann | ........................... | 607/30 |
| 6,605,094 B1 * | 8/2003 | Mann et al. | ................. | 606/129 |
| 6,609,029 B1 * | 8/2003 | Mann et al. | .................. | 607/37 |

\* cited by examiner

*Primary Examiner*—Henry Bennett
*Assistant Examiner*—Fadi H. Dahbour
(74) *Attorney, Agent, or Firm*—Kenneth L. Green; Laura H. Bishop

(57) ABSTRACT

A moveable contact connector system provides easy lead insertion, lead retention, and reliable electrical connection for implantable devices. The connector system may be used with in-line leads commonly found in such applications. Moveable contacts are provided in the connector, which contacts are placed in a first position for easy lead insertion, and in a second position for lead retention. The second position also provides a good electrical connection between the moveable connector contacts and the lead contacts. Multiple means for moving said at least one moveable contact between the first and second positions are described. A first embodiment uses a rotatable cam which is rotated to align the cam lodes with said at least one moveable contact, pushing the movable contacts against the lead contacts. The second and third embodiments use a sliding key to force said at least one moveable contact against the lead contacts.

44 Claims, 11 Drawing Sheets

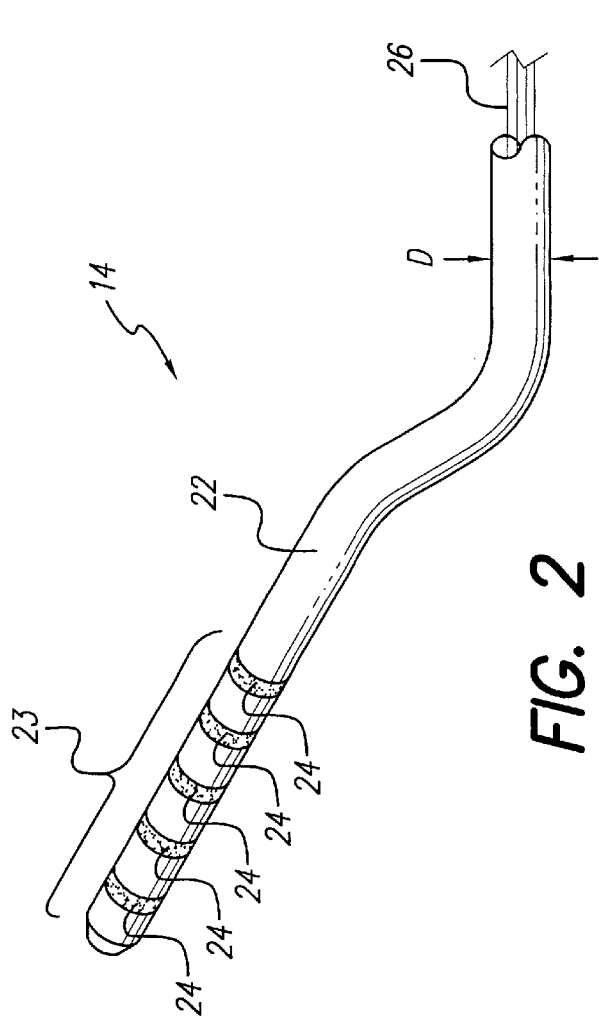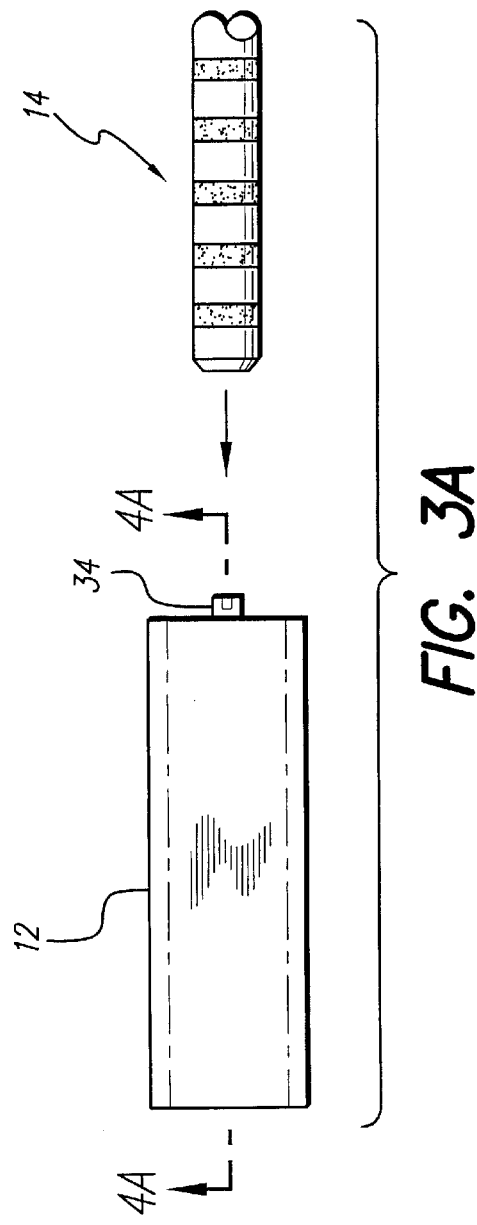

MOVABLE CONTACT LOCKING MECHANISM FOR SPINAL CORD STIMULATOR LEAD CONNECTOR

The present application claims the benefit of U. S. Provisional Application Serial No. 60/188,967, filed Mar. 10, 2000, which application is incorporated herein by reference.

BACKGROUND OF THE INVENTION

The present invention relates to implantable electronic and electrochemical medical devices and systems, and more particularly to a movable contact locking connector system for use with such devices and systems. Such connector system provides easy lead insertion, a reliable means to retain an in-line lead in a connector and ensures effective electrical connection between lead and connector contacts. The connector system provides these features through a simple design avoiding complexity.

Implantable electronic medical devices and systems have been in use for the past 20 years or more. One of the earliest implantable medical devices to be implanted in a patient was the cardiac pacemaker. Other implantable electronic devices have included neurostimulators, i.e., electrical stimulators designed to stimulate nerves or other tissue, sensors for sensing various physiological parameters or physical status of a patient, and therapeutic-delivery devices, e.g., pumps for delivering controlled amounts of medication. In more recent years, a tiny implantable cochlear stimulator has been developed that allows patients who are profoundly deaf to experience the sensation of hearing. Other tiny implantable sensors and neuro-stimulators are under development that will enhance the ability of a patient who is a recipient of such sensors or stimulators to walk, or to see, or to experience the use of other lost or impaired body functions.

Most of the implantable medical devices and systems described above require that at least one electrical lead be connected thereto in order for the device or system to perform its intended function. Such lead typically includes a plurality of insulated conductors, or wires, through which electrical signals may be delivered or sensed. At an end distal from an implantable electronic device, each of the insulated conductors usually terminates in one or more electrodes designed to be in contact with body tissue. A Spinal Cord Stimulation (SCS) system, for example, has an electrode array adapted for insertion into the spinal column of the patient. Such electrode array typically employs a multiplicity of electrode contacts, each of which must be individually electrically connected to the pulse generator circuitry housed within an Implantable Pulse Generator (IPG). The lead associated with such spinal cord stimulator thus carries the individual conductors that electrically connect the respective electrodes, to the implantable pulse generator, thus making up the spinal cord stimulation system.

In-line leads are often chosen to connect an electrode array to an implantable electronic device. The contacts of an in-line lead are spaced-apart rings on one or more ends of the lead. An important benefit of such in-line lead is that when the lead is used with a ring type electrode array of similar diameter, the lead and array combination may be inserted into a patient's spinal column using a large gauge needle. However, the use of a lead with such in-line male connector with a simple push-in female connector is limited by the ability to push the lead into a female connector passageway. The problem of in-line lead insertion has been addressed by U.S. Pat. No. 5,843,141 issued Dec. 1, 1998 for "Medical Lead Connector System." The '141 patent uses a tool to pull the lead end into the connector. However, the requirement to provide good electrical contact between the contacts on the lead and the contacts in the connector, and the need to provide a means for retaining the lead in the connector once inserted, work against easy insertion, and results in a requirement that the lead be sufficiently strong to resist tearing or stretching during insertion and extraction. Damaging a lead during the implanting or replacement of an implantable electronic device increases the complexity and medical risks associated with the required surgery. But, adding strengthening structure to the lead may be difficult and result in undesirable stiffening of the section of the lead where the lead exits the connector. What is therefore needed is an improved in-line connector system that allows easy insertion of an in-line lead into a connector, good retention of the lead once inserted, and reliable contact between the lead's contacts and the connector's contacts. Further, it is desirable that an improved in-line connector system, having these qualities, not compromise the beneficial properties which the lead would otherwise have.

SUMMARY OF THE INVENTION

The present invention addresses the above and other needs by providing a connector system with spaced-apart moveable contacts in the connector, and means for forcing the moveable connector contacts downward against spaced-apart lead contacts (for the purposes of this description, downward means toward the lead contacts, however, in actual use the connector may be arbitrarily rotated). The connector system may be integrated into the housing of an implanted device for the connection of a lead to the device. Advantageously, the connector system provides easy lead insertion, positive lead retention, and reliable electrical contact, without complexity.

In accordance with one aspect of the invention, there is provided a connector system including one or more spaced-apart moveable contacts in a connector, one or more spaced-apart lead contacts on an end of an in-line lead, and a means for applying downward force against the moveable contacts. When a lead in inserted fully into the connector passageway, the downward force causes the moveable contacts to move from a first position, wherein the moveable contacts are not pressing against the lead contacts, to a second position, wherein the moveable contacts are pressing against the lead contacts. When the movable contacts are in the second position, sufficient force is applied to the moveable contacts by the means for applying downward force, to both retain the lead in the connector, and to provide reliable electrical connection between the moveable contacts and the lead contacts.

It is also a feature of the present invention to provide a connector body made from a resilient material. One or more moveable contacts are molded into the resilient connector body so that, in the absence of force, the moveable contacts rest in a position which permits easy insertion and removal of the lead. When force is applied to the moveable contacts by the means for applying downward force, the moveable contacts press against the lead contacts, thus retaining the lead, and providing reliable electrical contact between the connector contacts and the lead contacts. When the downward force is no longer applied to the moveable contacts, the resilient nature of the connector body causes the moveable contacts to return to the first position, thus freeing the lead.

It is a further feature of the invention to provide a solid cam with solid lobes as a means for applying downward force. The cam may be rotated, and the solid lobes thereby apply force to the moveable contacts, which force results in the moveable contacts moving from the first position to the second position. A cam stop lug is provided on the cam that cooperates with a cam stop in the connector to limit the rotation of the cam. The positions of the cam lug and the cam stop are designed to allow the cam to rotate to a locked position slightly past centering the solid lobes on the moveable contacts. As the cam is rotated from an open position to a locked position, the cam solid lobe pushes down on the moveable contacts. As the cam solid lobes rotate downward and against the moveable contacts, the resisting force of the movable contacts against the cam solid lobes result in torque on the cam resisting the rotation from the open to the locked position. When the cam lobes are pointed directly down (i.e., towards the moveable contacts) the moveable contacts, the solid lobes, and the rotational axis of the cam are aligned. In this position there is no torque on the cam. When the cam is rotated slightly farther, the torque on the cam is reversed and is pushing the cam towards the locked position. A past center effect thus results that causes the cam to remain in the locked position until sufficient torque is applied to force the solid lobes past centering the solid lobes on the moveable contacts. In a preferred embodiment the cam is a straight shaft with solid lobes spaced along the shaft. In an alternative embodiment the cam is a simple wireform device.

In a first alternative embodiment of the means for applying downward force, a rod with bulged sections is inserted into the connector. When the rod is fully inserted, the bulged sections align with the moveable contacts, thus applying force to move the moveable contacts from the first position to the second position. Advantageously, the bulged sections may be radially symmetric which allows the rod to be inserted with arbitrary rotation. In a variation of this embodiment, the rod is captive with a first and second position, wherein the bulges are not aligned with the movable contacts in the first position, allowing easy lead insertion; and the bulges are aligned with the movable contacts in the second position, providing good lead retention.

In a second alternative embodiment of the means for applying downward force, a moveable actuator is captive within the connector. The actuator defines one or more bulges vertically aligned with the moveable contacts. The actuator is free to move vertically within the connector. A key is insertable into the connector through a key passageway above the actuator. When the key is inserted, a ramped surface on the bottom face of the key pushes downward against the actuator causing the actuator to move downward against the moveable contacts, and thus causing the moveable contacts to move from the first position downward to the second position.

In a third alternative embodiment of the means for applying downward force, the single actuator and moveable contacts combination is replaced by individual second actuators cooperating with each movable contact. When the key is inserted, the key's ramped bottom surface pushes against the second actuators, thus causing the second actuators to move downward and push downward on the moveable contacts. The force of the second actuators on the moveable contacts causes the moveable contacts to move from the first position to the second position. In an alterative to this embodiment, the second actuators and moveable contacts are combined to form second movable contacts. The base of the second movable contact is resiliently molded into the connector body to allow vertical movement of the second moveable contacts and to retain the second moveable contacts in the connector body.

BRIEF DESCRIPTION OF THE DRAWINGS

The above and other aspects, features and advantages of the present invention will be more apparent from the following more particular description thereof, presented in conjunction with the following drawings wherein:

FIG. 2 shows an in-line lead used with the present invention;

FIG. 3A provides a top view of a connector system;

Corresponding reference characters indicate corresponding components throughout the several views of the drawings.

DETAILED DESCRIPTION OF THE INVENTION

Figure 1B:
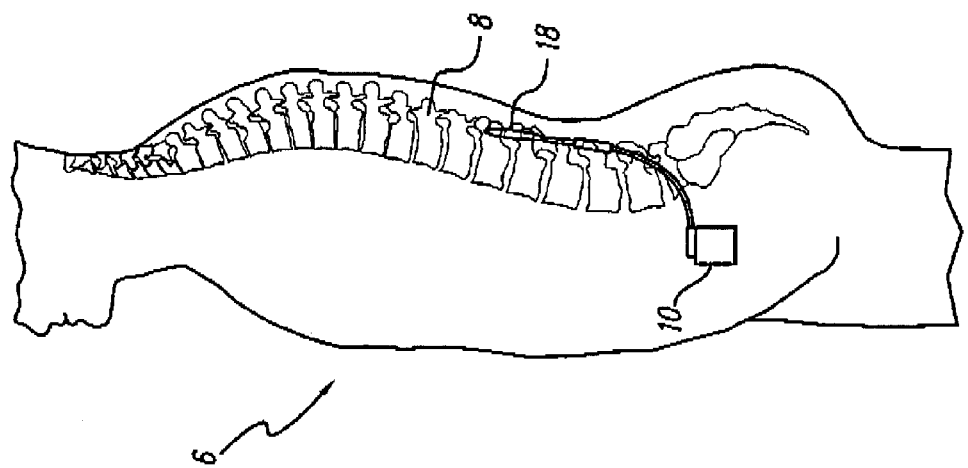
FIG. 1B depicts the SCS system of FIG. 1 implanted in a patient.

The following description is of the best mode presently contemplated for carrying out the invention. This description is not to be taken in a limiting sense, but is made merely for the purpose of describing the general principles of the invention. The scope of the invention should be determined with reference to the claims.

The connector system of the present invention provides a simple method for inserting, retaining, and ensuring reliable electrical contact for a multi-contact in-line lead and a connector. Such connector system is typically used in implanted medical devices, for example, in a Spinal Cord Stimulation (SCS) system 4 as shown in FIG. 1A. An SCS system 4 typically includes an Implantable Pulse Generator 10, a connector 12, an in-line lead 14, an in-line connector 16, an electrode lead 20, and an electrode array 18. The IPG 10 generates stimulation current for implanted electrodes that make up the electrode array 18. A connector 12 is either attached to the body of the IPG 10, or integrated into the IPG 10. The in-line lead 14 is removably connected to the connector 12 and either permanently or removably connected to the in-line connector 16, at the end of the in-line connector 16 proximal to the IPG 10, and the electrode lead 20 is removably connected to the end of the in-line connector 16 distal from the IPG 10. The electrode array 18 is typically formed on an end of the electrode lead distal from the in-line connector 16. The in-series combination of the in-line lead 14, in-line connector 16, and electrode lead 20, carry the stimulation current from the IPG 10 to the electrode array 18.

Figure 1A:
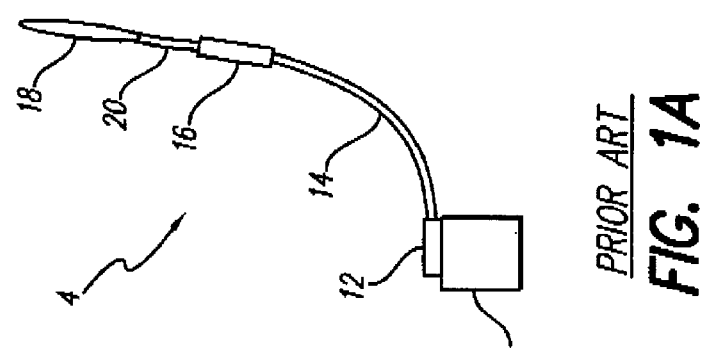
FIG. 1A shows a detailed view of a typical Spinal Cord Stimulation (SCS) system, the system comprising an electrical sensor/stimulator device connected to a lead having an electrical contact or an electrical array at its distal end.

A view of the SCS system 4 described in FIG. 1A above is depicted implanted in a patient 6 in FIG. 1B. The electrode array 18 (or sensors in other applications) is implanted at the site of nerves that is the target of stimulation, e.g., along the spinal column 8. Due to the lack of space where the electrode lead 20 exits the spinal column, the IPG 10 is generally implanted in the abdomen or above the buttocks. The in-line lead 20 facilitates locating the IPG 10 distal from the electrode lead exit point. The connector system of the present invention is particularly well suited for use with an IPG 10 because a small diameter lead is easier to pull through tissue than a large diameter lead, and the present invention facilitates the use of such small diameter lead.

The connector system of the present invention may be employed with various other implantable devices. Sensing devices have similar electrodes, leads, and implantable electronics. Any medical device requiring leads to connect sensors or stimulators to implantable electronics may benefit from the improved connector system.

The present invention is directed to implantable connector systems using an in-line lead 14 as shown in greater detail in FIG. 2. The in-line lead 14 typically has a constant diameter D, which enables the lead to be implanted through a large gauge needle. A constant or uniform diameter D is particularly useful for an electrode lead 20 attached to a ring type electrode array of an SCS system 4. In such case, the entire electrode array and electrode lead assembly are the same diameter, thus permitting the entire assembly to be implanted through a large gauge needle.

As seen in FIG. 2, an in-line lead 14 comprises a lead body 22, at least one conductor 26 carried within the lead body 22, and at least one spaced-apart lead contact 24 on the lead body 22. A lead end 23 in inserted into the connector 12 to electrically connect the in-line lead 14 to the connector 12. It is through the lead contacts 24 that electrical connection is made between each of the conductors 26 that are carried within the in-line lead 14 and the electrical circuit in the IPG 10, or with the conductors of the in-line connector 16. The in-line lead 14 may have identical ends (only one of which is shown in FIG. 2) with spaced-apart lead contacts 24, or may have one end as depicted in FIG. 2, and the opposite end may be a female connector. In other cases, as with the electrode lead 20, one end is as depicted in FIG. 2 and the opposite end includes the electrode array/sensors.

While the implantable system depicted in FIGS. 1A and 1B comprises a separate lead 14 connecting the electrode lead 20 to the IPG 10, a connector made according to the present invention would apply equally well to a system with an electrode lead connected directly to the IPG 10.

The in-line lead 14 may be manufactured using conventional lead manufacturing techniques and materials, as are known and practiced in the implantable lead art.

Figure 3:
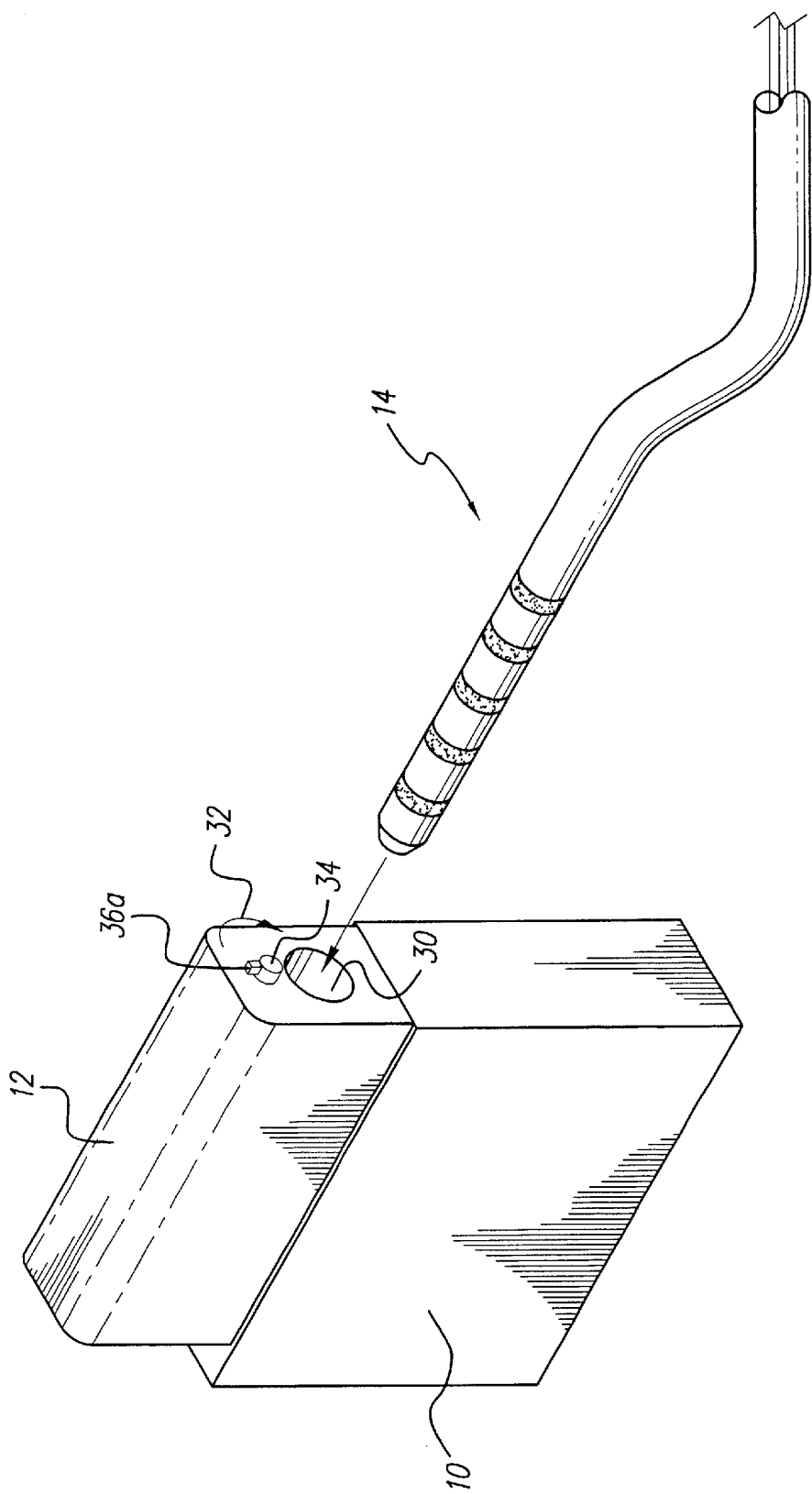
FIG. 3 illustrates a rotating lock connector system according to the present invention, integrated into an implantable device.

Turning to FIG. 3, a connector according the present invention is shown integrated into the IPG 10. The lead 14 is insertable through a connector port 30. The rearward end of a solid cam 34, which solid cam 34 serves as a means for locking the lead 14 into the connector 12, protrudes from the connector 12 just above the connector port 30. The solid cam 34 has a handle lug 36 attached to the rearward end, which handle lug 36 provides means to removably connect a key or handle to the solid cam 34 for the purpose of rotating the solid cam 34, as indicated by the arrow 32.

A top view of the connector 12 is shown in FIG. 3A for the purpose of defining cross-section 4A—4A.

Figure 4:
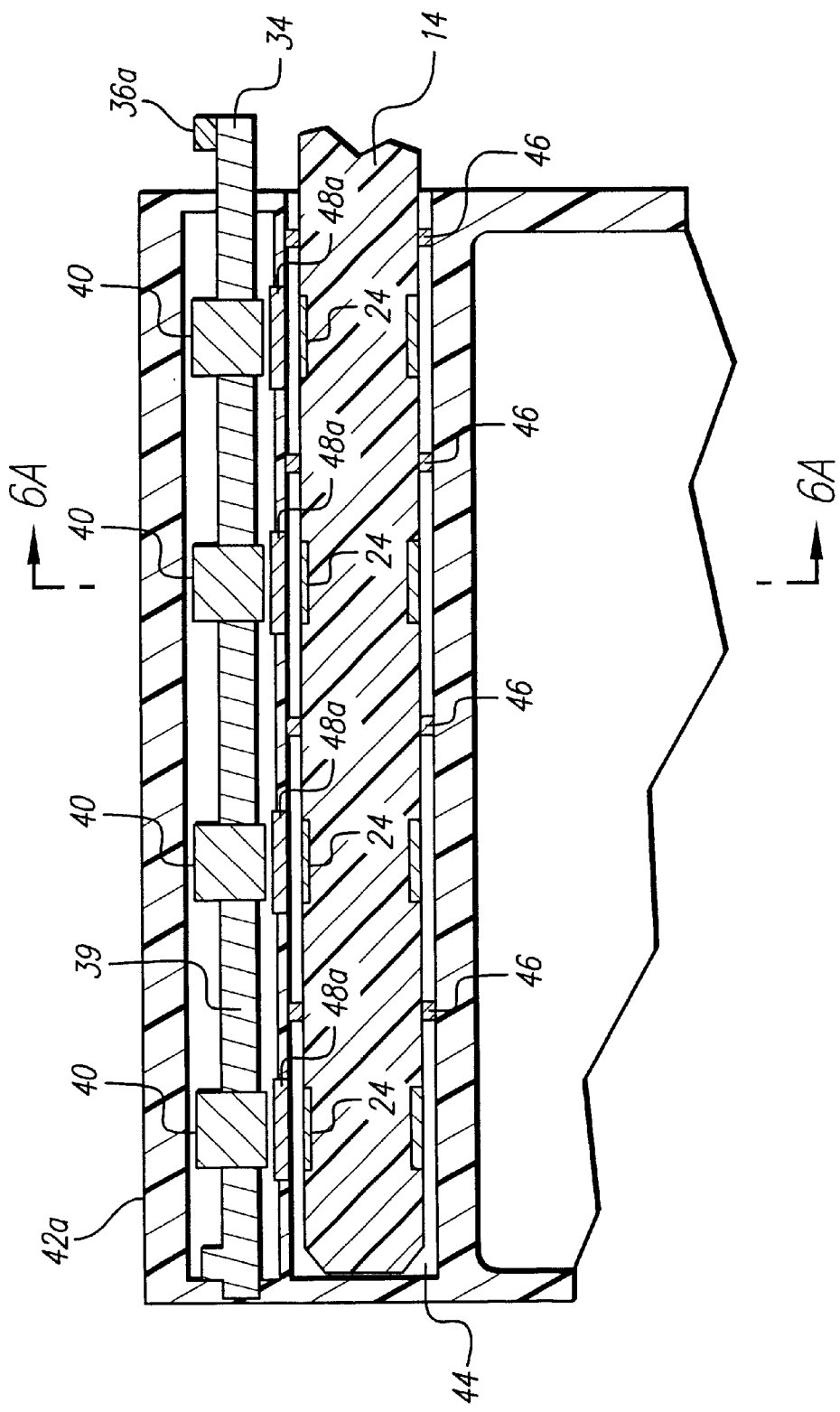
FIG. 4 shows a cross-sectional view of the connector taken along line 4A—4A of FIG. 3A, with moveable contacts in a first position.

A cross-sectional view of the connector 12 taken at line 4A—4A of FIG. 3A is shown in FIG. 4. The in-line lead 14 is shown fully inserted through connector port 30, shown in FIG. 3, into a cylindrically shaped passageway 44. In the example shown, the in-line lead 14 has four spaced-apart lead contacts 24. The actual number of contacts may vary and is not limited by this description. At least one spaced-apart movable contact as 48a is molded into the portion of a connector body 42a that forms the wall of the passageway 44. The movable contacts 48a are vertically aligned with the respective lead contacts 24 with which each of the moveable contacts 48a cooperates. The connector body 42a is made from a resilient material, preferable epoxy. The first moveable contacts 48 are molded into the connector body 42a so that in the absence of a downward force (within this description "downward" means toward the lead contacts 24; however, in use, the connector may be arbitrarily rotated) upon the moveable contacts 48, the in-line lead 14 may be easily inserted completely into the passageway 44. When a downward force is applied to the moveable contacts 48, the resilient connector body 42a allows the moveable contacts 48 to be pushed against the lead contacts 24. The solid cam 34 comprises a substantially straight shaft 39 and at least one solid lobe 40. The solid cam 34 shown in FIG. 4 has the at least one solid lobe 40 pointing away from the movable contacts 48a. As a result, the movable contacts 48a are in a relaxed position, wherein they are not pressing against the lead contacts 24, thus permitting easy insertion of the in-line lead 14. The handle lug 36 is also shown pointing up. In this embodiment the handle lug 36 is aligned with the solid lobes 40 to provide an intuitive indication of the direction of the solid lobes 40. While this is an advantageous alignment, the handle lug 36 may be aligned arbitrarily without departing from the scope of the invention.

In a preferred embodiment, the moveable contacts 48 are resiliently attached to the connector body 42a in a manner to cause the moveable contacts 48 to retreat from the lead contacts 24 when no downward force is acting on the moveable contacts 48. In such cases, the moveable contacts rest in a first cam position when no force is applied to them. When the downward force is applied to the moveable contacts 48, the moveable contacts 48 move to a second cam position where they contact the lead contacts 24. In other embodiments, the absence of a downward force upon the moveable contacts 48 may result in the moveable contacts touching but applying negligible force to the lead contacts 24. In either case, the absence of a downward force applied to the movable contacts 48a results in easy insertion and removal of the lead end 23 from the connector 12.

In a preferred embodiment, the lead contacts 24 comprise rings that circle the lead body 22 as shown in FIG. 2. The cross-sectional view of the lead contacts 24 shown in FIG. 4 shows the rectangular cross sections of the lead contacts 24 at the top and bottom of the in-line lead 14. In other embodiments the cross-sectional view of the lead contacts 24 may be rounded or "D" shaped. These other cross-sections are intended to come within the scope of the present invention. Connector ridge seals 46 are molded into the passageway 44 to prevent conductive body fluids from readily passing between connectors and to thereby minimize current leakage between contacts. The connector seals 46 form a complete circle around the inner diameter of the passageway 44, much like an o-ring, and make sufficient contact with the lead body 22 to prevent fluid and current leakage.

Figure 5:
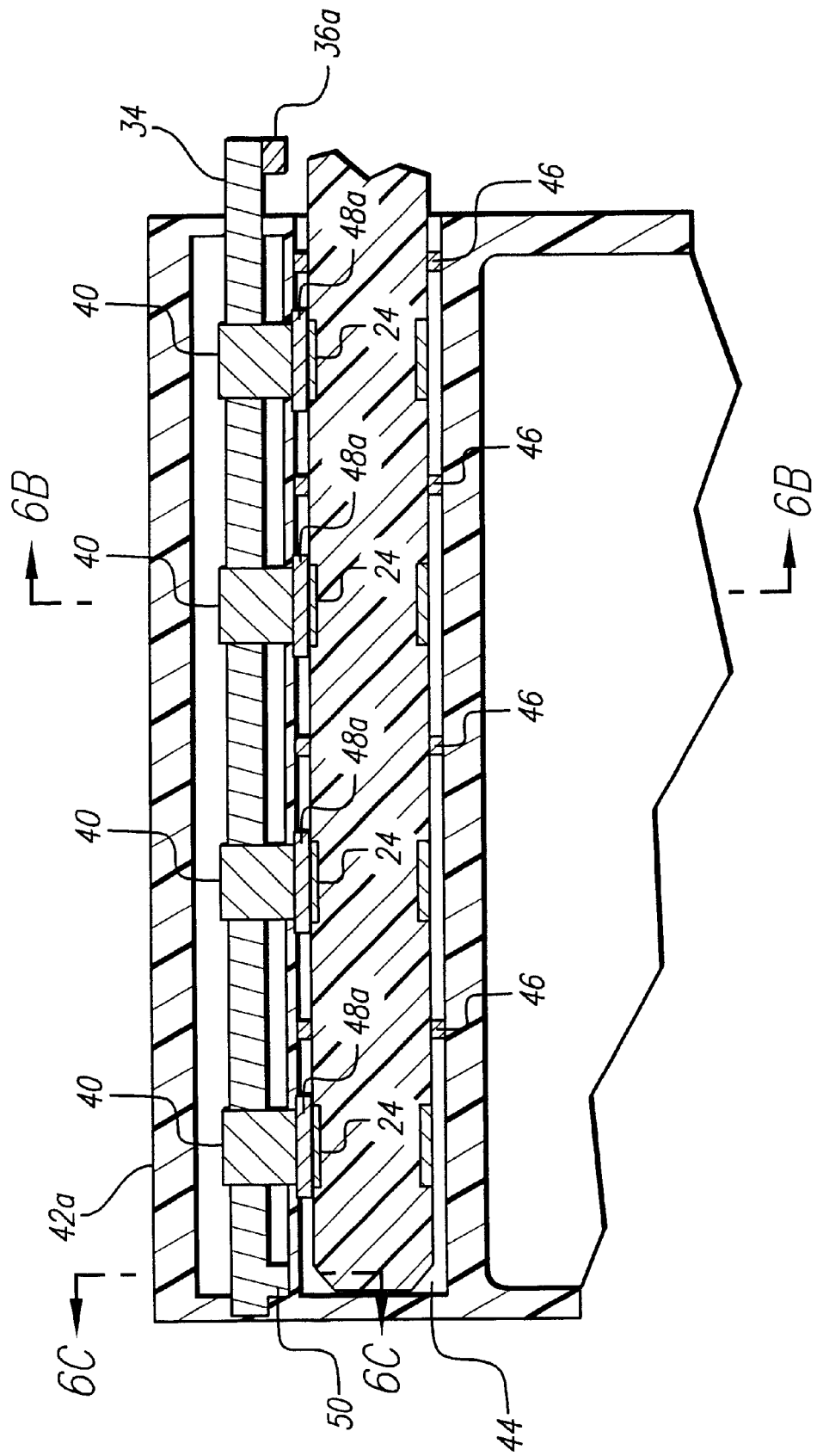
FIG. 5 shows a second cross-sectional view of the connector taken along line 4A—4A of FIG. 3A, with moveable contacts in a second position.

A second sectional view taken at line 4A—4A of FIG. 3A is shown in FIG. 5. This view is identical to the view in FIG. 4 with the exception that the solid cam 34 has been rotated approximately 180 degrees into a locking position. The handle lug 36 is in the down position. The solid lobes 40 are now pointing down and contacting the moveable contacts 48. The moveable contacts 48 are pushed down and are contacting the lead contacts 24. In this position, the in-line lead 14 is held in the passageway 44 by the friction resulting from the moveable contacts 48 pushing against the lead contacts 24. A reliable electrical connection is created by the same cooperation of contacts. A cam stop lug 50 resides on the forward end of the solid cam 34.

Figure 6C:
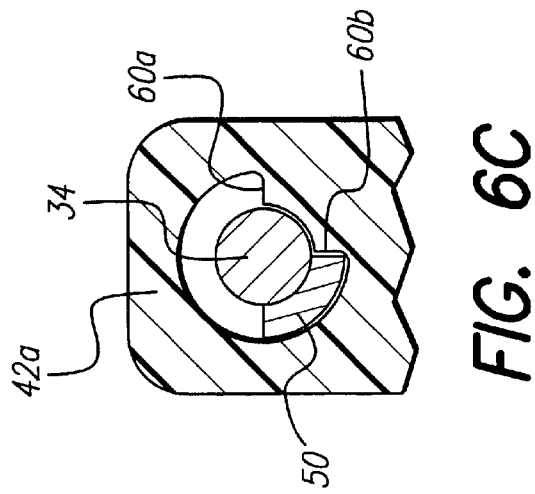
FIG. 6C shows a cross-sectional view of the connector taken along line 6C—6C of FIG. 5.
Figure 6B:
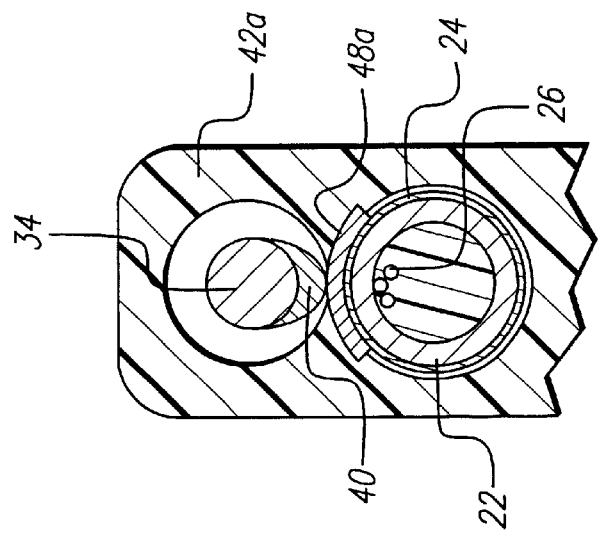
FIG. 6B shows a cross-sectional view of the connector taken along line 6B—6B of FIG. 5.
Figure 6A:
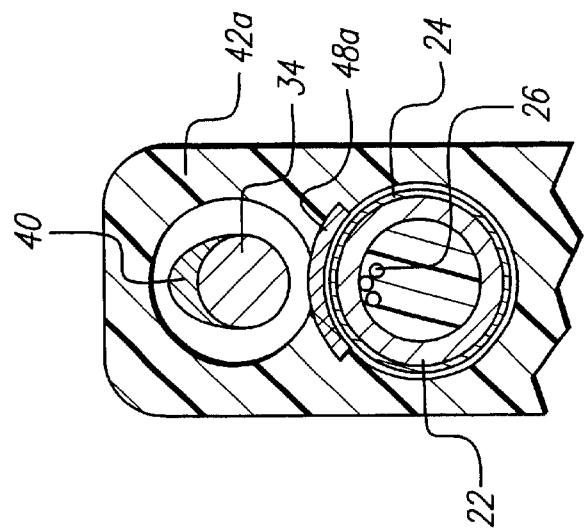
FIG. 6A shows a cross-sectional view of the connector taken along line 6A—6A of FIG. 4.

A cross sectional view taken at line 6A—6A of FIG. 4 is shown in FIG. 6A. The arced shape of the moveable contacts 48 is clearly visible. Additionally, the conductors 26 are shown within the lead body 22. The solid lobes 40 are pointed up and are not in contact with the moveable contacts 48. In the absence of downward force, the moveable contacts 48 are not touching the lead contacts 24.

A cross sectional view taken at line 6B—6B of FIG. 5 is shown in FIG. 6B. The solid lobes 40 are pointed downward and are pushing the moveable contacts 48 firmly against the lead contacts 24.

Another cross sectional view taken at line 6C—6C of FIG. 5 is shown in FIG. 6C. The solid cam 34 is depicted in the locked position (i.e., the solid lobes 40 are pointing downward towards the moveable contacts 48 as shown in FIG. 6B.) The cam stop lug 50, on the forward end of the solid cam 34, is resting against a second cam stop 60b, thus providing a second rotational stop for the solid cam 34 and a closed position for the connector 12. The cam stop lug 50 and cam stop 60b are designed to allow the solid cam 34 to rotate slightly past the point where the solid lobes 40 are pointed directly at the moveable contacts 48. By incorporating this "past center" position, the solid cam remains in the locked position once released. The solid cam 34 may be rotated so that the cam stop lug 50 cooperates with a first cam stop 60a thus providing a first rotational stop for the solid cam 34 an open position for the connector 12. While the cam stop lug 50 is shown at the forward end of the solid cam 34, other locations for the cam stop lug 50 along the length of the solid cam 34 will provide an equivalent function, and are intended to come within the scope of the present invention.

Figure 7:
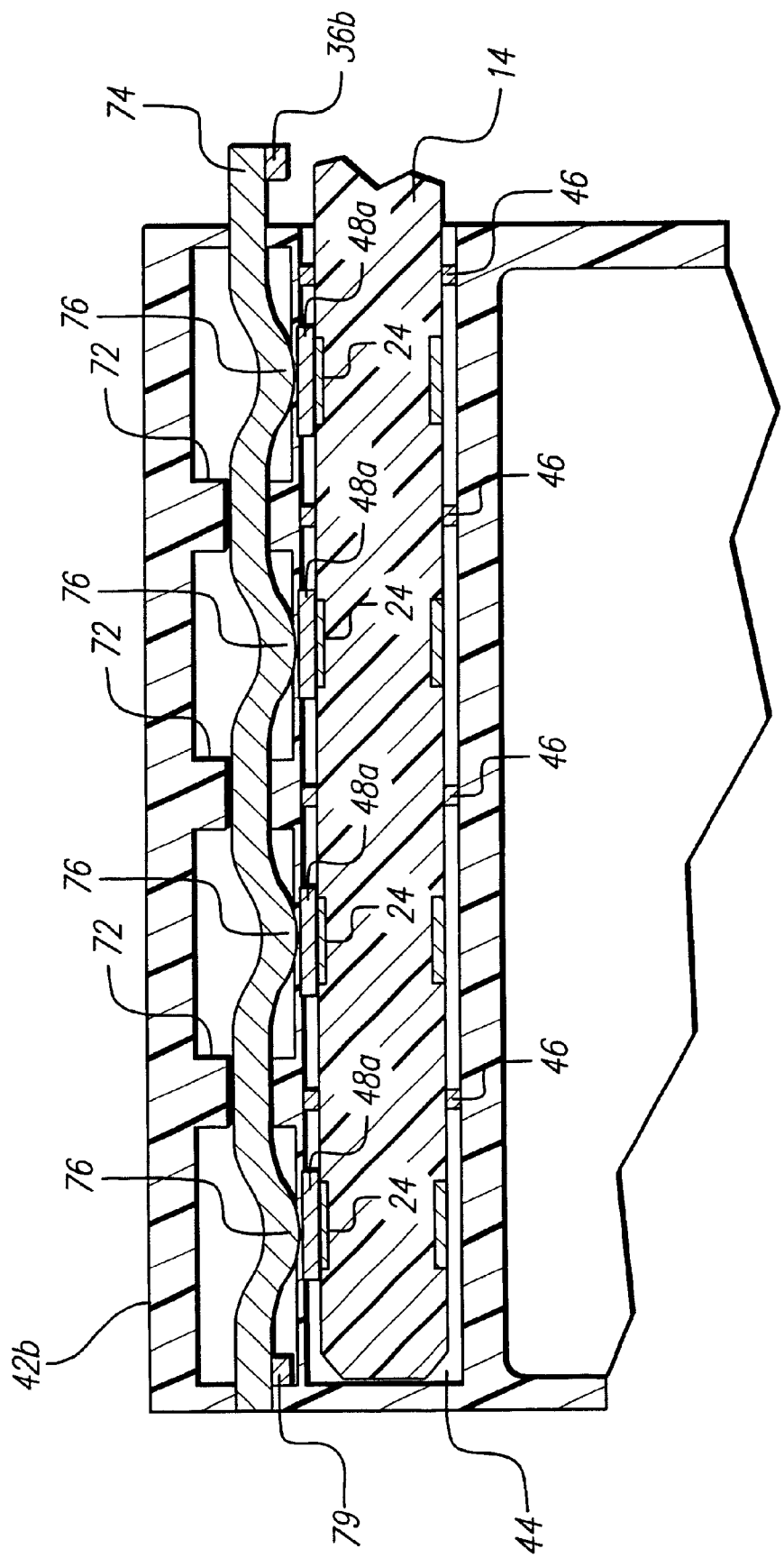
FIG. 7 illustrates a second embodiment of a rotating lock, with a bent wire cam.

Turning to FIG. 7, and alternative embodiment of a cam serving as a means for applying downward force on the moveable contacts is shown. A wireform cam 74 is inexpensively formed from wire. Wireform lobes 76 press down on the moveable contacts 48 to provide downward force. At least one cam support 72 in a second connector body 42b is provided to rotatably support at least one straight section of the wireform cam 74. The support provided by the at least one cam support 72 allows the wireform cam to be rotated about an axis substantially parallel with the passageway 44. The handle lug 36 provides a means to turn the wireform cam 74 in the same manner as the handle lug 36 in FIG. 3. A cam stop lug 50 provides a positive rotational stop for the second solid cam as in the case of the solid cam 34 illustrated in FIG. 6C. The wireform cam 74 functions substantially the same as the solid cam 34 described in FIGS. 4, 5, and 6.

Figure 8:
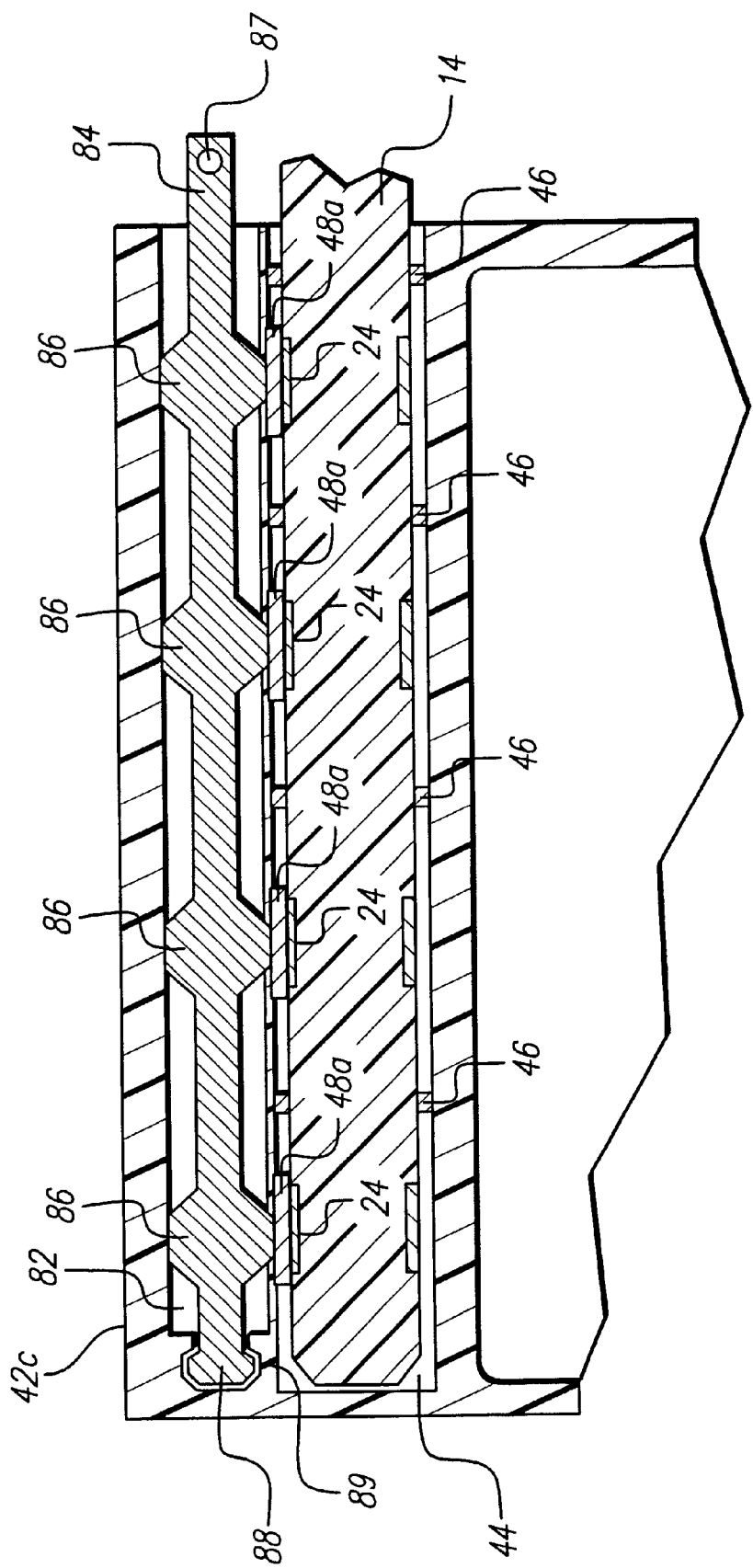
FIG. 8 depicts a first alternative embodiment of a means for applying a downward force.

An alternative to the solid cam 34 of FIG. 4 is shown in FIG. 8. A removable rod 84 is inserted into a rod passageway 82 in a third connector body 42c as a means for applying downward force on the moveable contacts 48. In a preferred embodiment, the removable rod 84 defines radially symmetric bulges 86 at the same spacing as the spaced-apart moveable contacts 48. Advantageously, the symmetry of the bulges permits the removable rod to be inserted with an arbitrary rotation. Alternative embodiments may include asymmetric bulges, with a key way, or equivalent means, to align the asymmetric bulges with the moveable contacts 48a. When the removable rod 84 is fully inserted into the rod passageway 82, the symmetric bulges 86 are aligned with the moveable contacts 48, and push the moveable contacts 48 downward against the lead contacts 24. The resulting cooperation between contacts both retains the in-line lead 14 in the passageway 44, and provides a reliable electronic connection between the contacts. A rod latch 88 is provided on a forward rod end opposite the exposed rearward end of the removable rod 84. A cooperating latch receptacle 89, constructed from the resilient connector body 42c material, is molded into the rod passageway 82. When the removable rod 84 is pushed fully into the rod passageway 82, the rod latch 88 snaps into the latch receptacle 89 to latch the removable rod 82 into the connector body 42c. A hook hole 87 is provided on an exposed rearward end of the removable rod 84 to provide means to pull the removable rod from the connector body 42c. The latch described in FIG. 8 is one example of many equivalent means for providing retention of a rod in a rod cavity.

In another variation, the rod may be captive within the connector. The rod would require sufficient freedom to be moved from a first rod position where the bulges are not aligned with the moveable contacts, to a second rod position where the bulges are aligned with the moveable contacts. Such variations will be apparent to those skilled in the art and are intended to fall within the scope of the present invention.

Figure 9:
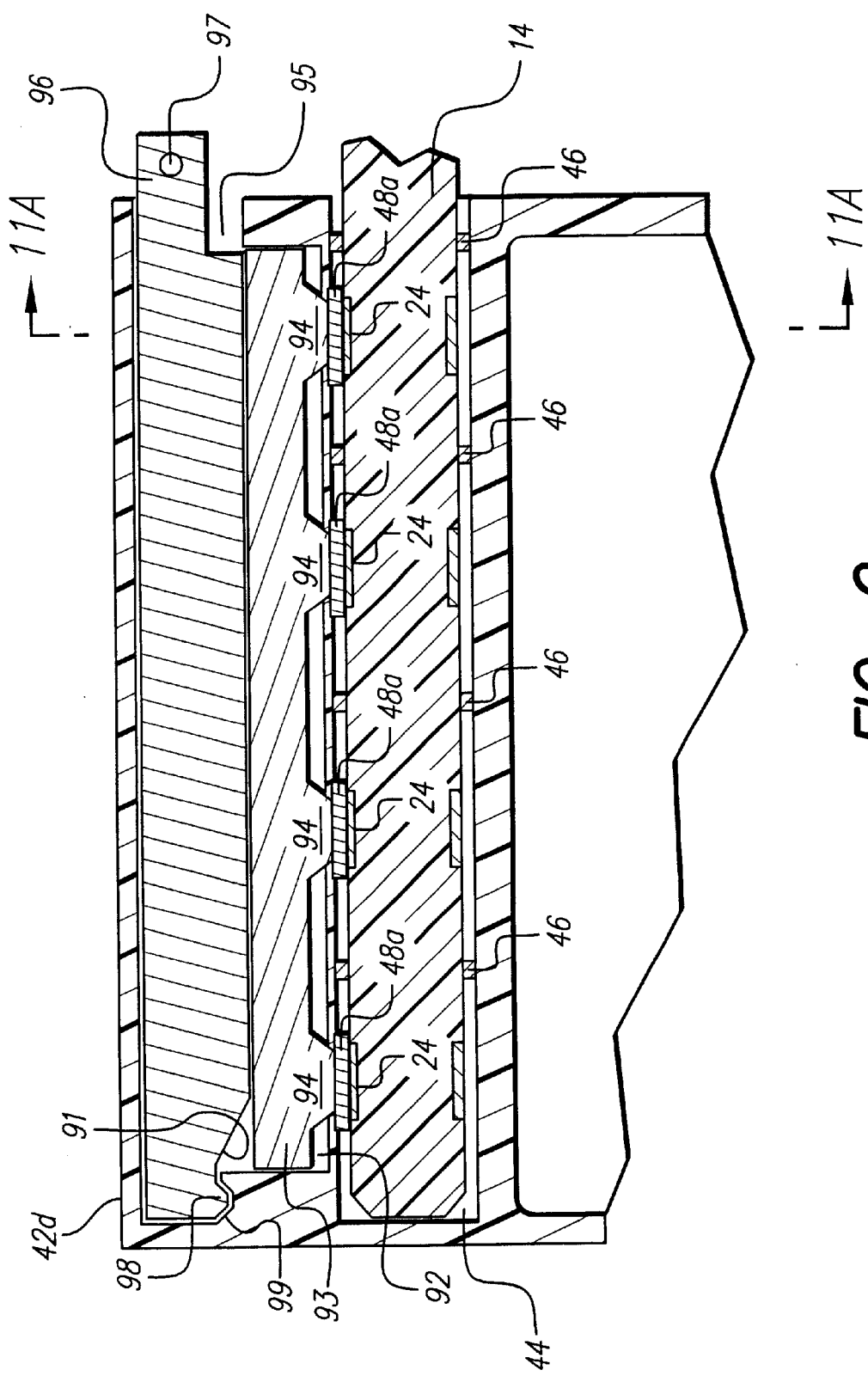
FIG. 9 depicts a second alternative embodiment of a means for applying a downward force.

A second alternative embodiment of the connector is shown in FIG. 9. A fourth connector body 42d comprises the passageway 44 as shown in previously described embodiments, but further comprises an actuator cavity 92 and a key passageway 95. A captive actuator 93 is positioned in the actuator cavity 92 above the moveable contacts 48 as a means for applying downward force on the moveable contacts. The captive actuator 93 defines bottom bulges 94 which are vertically aligned with the movable contacts 48a. The captive actuator 93 is limited to vertical motion only. A removable key 96 is removably insertable into the key passageway 95 above the captive actuator 93. A fully inserted removable key 96 has a rearward end that protrudes from the connector body 42d, and a forward end opposite the rearward end. The bottom of the removable key 96 defines a short downward ramp 91 at the forward end followed by a straight section. When the forward end of the removable key 96 is first inserted into the key passageway 95, the downward ramp 91 makes contact with the captive actuator 93, and the captive actuator 93 is pushed down against the moveable contacts 48. The resulting downward force of the moveable contacts 48 against the lead contacts 24 retains the in-line lead 14 in the passageway 44, and provides a reliable electronic connection between the contacts. When the removable key 96 is fully inserted into the key passageway 95, a key latch 98 on the forward end of the removable key 96, snaps into a latch receptacle 99 to retain the removable key 96 in the key passageway 95. A hook hole 97 is provided in the rearward end of the removable key 96 to facilitate the removal of the removable key.

Figure 10:
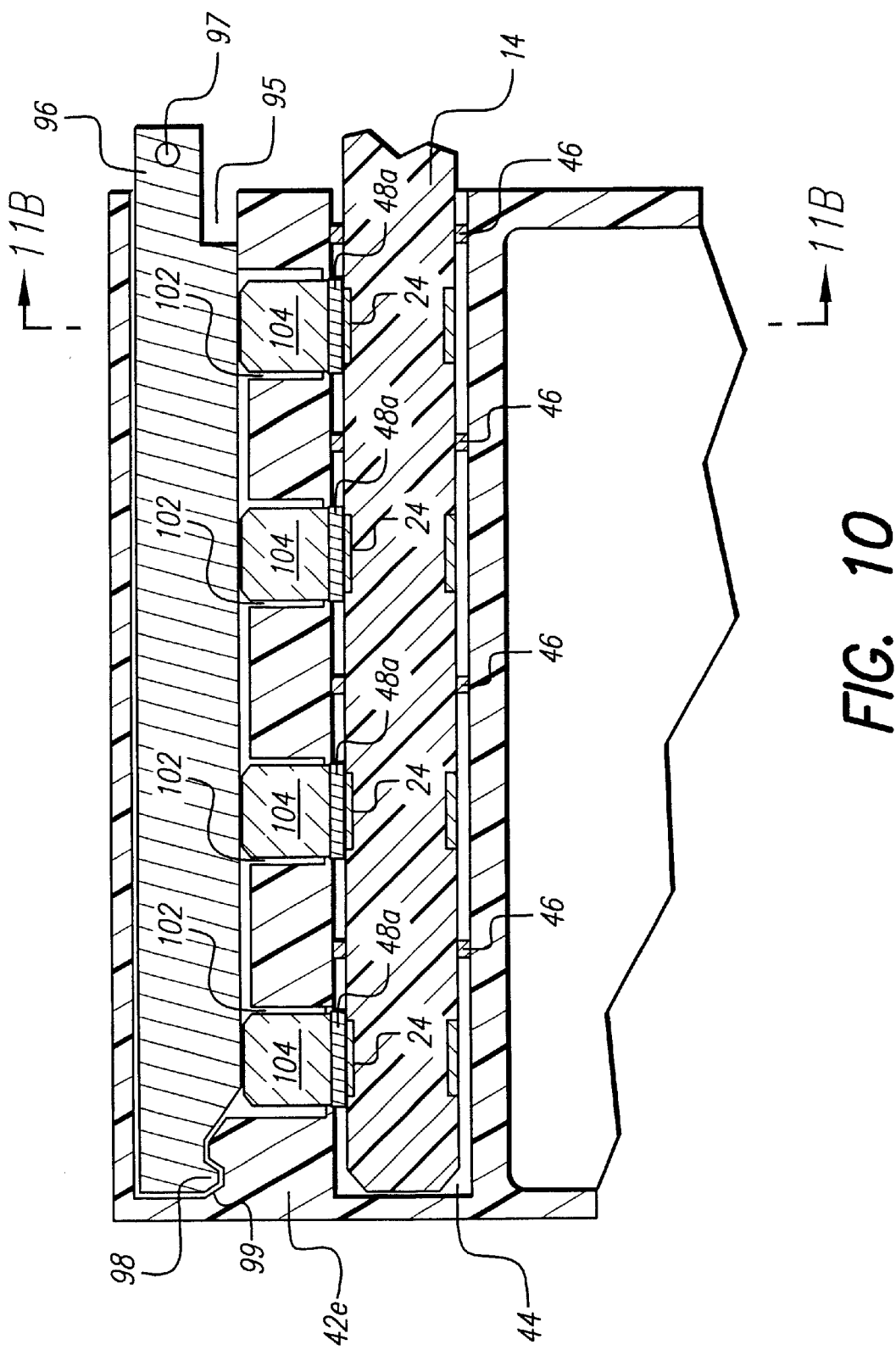
FIG. 10 depicts a third alternative embodiment of a means for applying a downward force.

A third alternative embodiment of the connector is shown in FIG. 10. A fifth connector body 42e comprises the passageway 44 and the key passageway 95 as shown in FIG. 9, but further comprises at least one actuator guide 102. At least one multi actuator 104 slidably resides in the actuator guides 102. The multi actuators 104 preferably have a round or rectangular horizontal cross section, but variations of the cross section will be apparent to those skilled in the art and fall within the scope of the present invention. The actuator guides 102 allows vertical movement of the multi actuators 104 but limit horizontal movement. The multi actuators 104 are positioned directly above the movable contacts 48a. The removable key 96 as described in FIG. 9 or equivalent, is insertable into the key passageway 95 above the multi actuators 104 as a means for applying a downward force on the multi actuators 104. The bottom of the removable key 96 defines the downward ramp 91 followed by a straight section. The straight section is sufficiently long to cover all of the multi actuators 104 when the removable key 96 is fully inserted into the key passageway 95. When the downward ramp 91 on the bottom of the removable key 96 makes contact with the multi actuators 104, the multi actuators 104 are pushed down against the moveable contacts 48. The moveable contacts 48 then are pushed down against the lead contacts 24. The resulting downward force both retains the in-line lead 14 in the passageway 44, and provides a reliable electronic connection between the contacts.

Figure 11C:
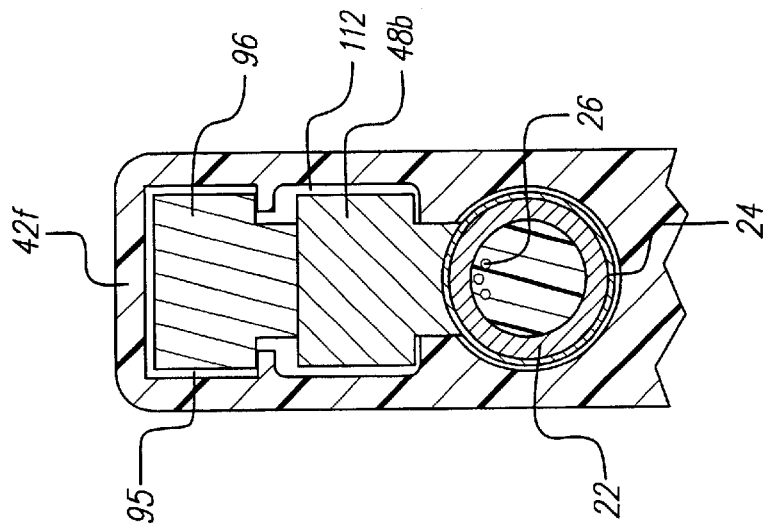
FIG. 11C shows a cross-sectional view of a variation of the third alternative embodiment, taken along line 11B—11B of FIG. 10.
Figure 11B:
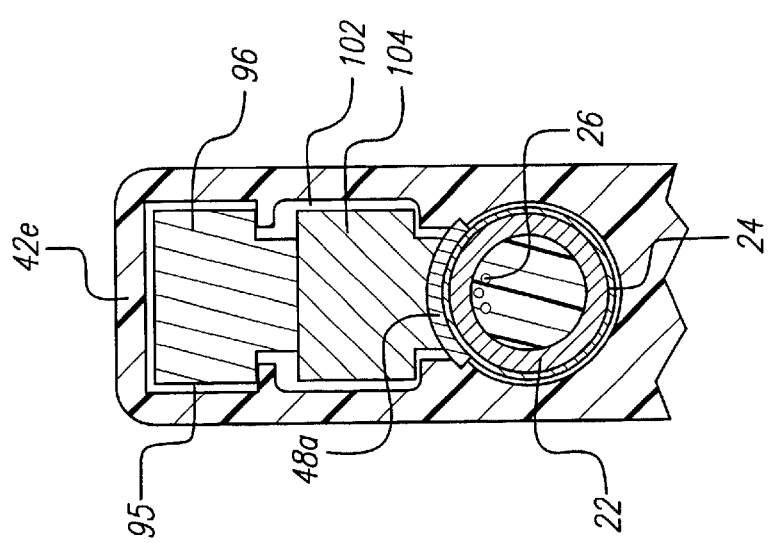
FIG. 11B shows a cross-sectional view of the third alternative embodiment, taken along line 11B—11B of FIG. 10.
Figure 11A:
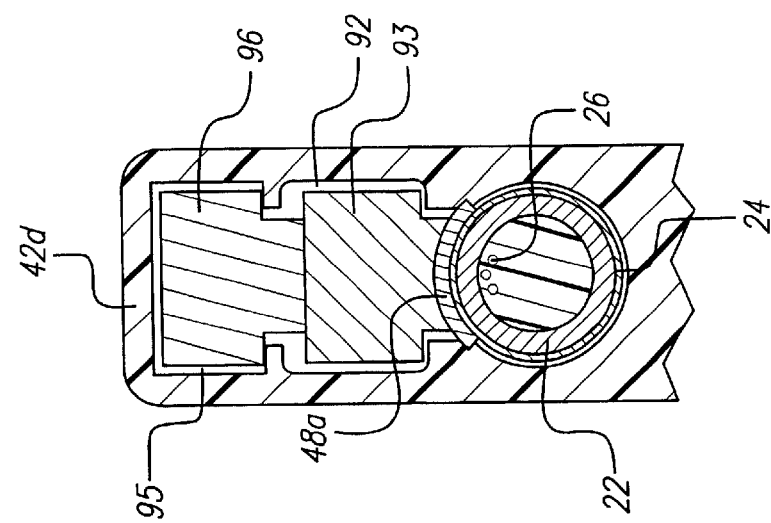
FIG. 11A shows a cross-sectional view of the second alternative embodiment, taken along line 11A—11A of FIG. 9.

FIGS. 11A and 11B are cross sectional views taken along the lines 11A—1A of FIG. 9 and the lines 11B—11B of FIG. 10, respectively. FIG. 11A shows a second cross section of the second alternative embodiment of the means for applying downward force on the moveable contacts 48. In this view, the removable key 96 is seen in the key passageway 95. The captive actuator 93, in the actuator cavity 92, is just below the removable key 96, and is forced downward by the removable key. The captive activator 93 forces the moveable contacts 48 downward. The moveable contacts 48 are thus pushed against the lead contacts 24. The resulting downward force both retains the in-line lead 14 in the passageway 44, and provides a reliable electronic connection between the contacts.

FIG. 11B is nearly identical to FIG. 11A with the exception that the captive actuator 93 in the actuator cavity 92 of FIG. 11A is replaced by the multi actuators 104 in the actuator guides 102 in FIG. 11B. The actuator guides 102 position the multi actuators 104 above the movable contacts 48a and limit the multi actuators 104 to vertical movement. The removably insertable removable key 96 applies a downward force on the multi actuators 104. The multi actuators 104 push down on the moveable contacts 48. The moveable contacts 48 are thus pushed against the lead contacts 24. The resulting downward force both retains the in-line lead 14 in the passageway 44, and provides a reliable electronic connection between the contacts.

A connector with a second at least one spaced-apart moveable contact 48b is shown in FIG. 11C. The moveable contacts 48b replace both the multi actuators 104 and first moveable contacts 48a shown in FIG. 11B described above. The moveable contacts 48b are movably contained in contact guides 112. The contact guides 112 are vertically aligned with the lead contacts 24 of a fully inserted lead end 23. The moveable contacts 48b are resiliently molded into a sixth connector body 42f at the base of the moveable contacts 48b. Such resilient molding allows the movable contacts 48b to be pushed against the lead contact 24 by the insertion of the removable key 96 into the key passageway 95, wherein the bottom key surface presses against at least one contact top surface, thereby retaining the lead end 23 in the connector body 42f. The same resilience causes the moveable contacts 48b to pull away from the lead end 23 when the removable key 96 is removed from the key passageway 95, allowing easy removal of the lead end 23 from the connector body 42f.

It is this seen that in each embodiment of the connector described herein, the moveable contacts are molded into the resilient connector body material to provide the correct positioning for the moveable contacts. A downward force moves the moveable contacts against the in-line lead. A resilient force moves the moveable contacts away from the in-line lead when no other force is acting upon the moveable contacts. This advantageously provides a simple connector, but alternative designs, for example using springs, would obtain the same functionality as that described here. Other means for positioning and restoring the moveable contacts will be apparent to those skilled in the art, and are intended to be within the scope of the present invention.

While the invention herein disclosed has been described by means of specific embodiments and applications thereof, numerous modifications and variations could be made thereto by those skilled in the art without departing from the scope of the invention set forth in the claims.

What is claimed is:

1. A connector system for use with implantable medical devices comprising:
    a connector body;
    a passageway in the connector body;
    a plurality of spaced-apart contacts moveable from a first, resting position into a second, downward position and resiliently attached to the connector body;
    a lead end, wherein the lead end is insertable into the passageway;
    a plurality of spaced-apart lead contacts residing on the lead end, wherein said lead contacts are respectively aligned with said moveable contacts when the lead end is fully inserted into the passageway; and
    means for applying a downward force on said moveable contacts by moving the moveable contacts from the first position into the second position to press the moveable contacts into the second position against the respective said lead contacts when the lead end is inserted into the passageway;
    wherein the lead end may be inserted into the passageway when the moveable contacts are in the first position and the downward force on the moveable contacts is not present, and wherein the lead end is held in the passageway and a reliable electrical connection is made between the moveable contacts and the lead contacts when the contacts are moved into the second position so the downward force on the moveable contacts is present.

2. The connector system of claim 1 wherein the connector is attached to an implantable electronic device.

3. The connector system of claim 2 wherein the implantable electronic device is an Implantable Pulse Generator (IPG).

4. The connector system of claim 1 wherein the lead end resides on an in-line lead.

5. The connector system of claim 1 wherein the lead end resides on an electrode lead.

6. A connector system comprising;
   a connector body;
   a passageway in the connector body;
   a moveable contact resiliently attached to the connector body;
   a lead end, wherein the lead end is insertable into the passageway;
   a lead contact on the lead end, wherein said moveable contact is respectively aligned with said lead contact when the lead end is fully inserted into the passageway; and
   a cam rotatably attached to the connector body, wherein the cam defines a lobe, and wherein said lobe is vertically aligned with said moveable contact, and wherein the cam has a first cam position wherein the lobe is pointed towards the moveable contact, thereby applying a downward force on said moveable contact to press the moveable contact against the lead contact, and wherein the cam has a second cam position wherein the lobe is pointed away from said moveable contact, thereby removing the downward force;
   wherein the lead end may be inserted into the passageway when the downward force on the moveable contact is not present, and wherein the lead end is held in the passageway and a reliable electrical connection is made between the moveable contact and the lead contact when the downward force on the moveable contact is present.

7. The connector system of claim 6 wherein the cam comprises a solid cam and the lobe comprises a solid lobe, wherein the solid cam has a substantially straight shaft, and wherein said solid lobe comprises a rounded solid body attached to the substantially straight shaft, and wherein the solid lobe is offset from the axis of the substantially straight shaft.

8. The connector system of claim 7 wherein the substantially straight shaft has a rearward end protruding from the connector body, and wherein a handle lug may be attached to the rearward end, wherein the handle lug may be used to attach a handle to rotate the solid cam.

9. The connector system of claim 7 wherein the solid cam includes a cam stop lug and wherein the connector body includes a first cam stop that cooperates with the cam stop lug to provide a first rotational stop for the solid cam in the first cam position, and wherein the connector body includes a second cam stop that cooperates with the cam stop lug to provide a second rotational stop for the solid cam in the second cam position.

10. The connector system of claim 9 wherein the second rotational stop allows the solid cam to be rotated just past the point where the solid lobe is pointed towards said moveable contact.

11. The connector system of claim 6 wherein the cam comprises a wireform cam, and wherein said lobe comprises a wireform lobe, wherein the wireform cam may be formed from a wire.

12. The connector system of claim 11 wherein the connector body includes a cam support, and wherein the wireform cam includes a straight section, wherein the cam support rotatably supports the straight section thereby allowing the wireform cam to rotate about an axis substantially parallel with the passageway.

13. The connector system of claim 12 wherein the wireform cam has a wireform rearward end protruding from the connector body, and wherein the wireform cam includes a handle lug attached to the wireform rearward end, which handle lug may be used to attach a handle to rotate the wireform cam.

14. The connector system of claim 12 wherein the wireform cam includes a cam stop lug, and wherein the connector body includes a first cam stop and a second cam stop, wherein the cam stop lug cooperates with the first cam stop to the second cam stop cooperate to provide a first rotational stop for the solid cam in the first cam position, and wherein the connector body includes a second cam stop that cooperates with the cam stop lug to provide a second rotational stop for the solid cam in the second cam position.

15. The connector system of claim 14 wherein the cam stop lug is attached to the wireform cam at a forward end of the wireform cam.

16. A connector system comprising;
   a connector body;
   a passageway in the connector body;
   a moveable contact resiliently attached to the connector body;
   a lead end, wherein the lead end is insertable into the passageway;
   a lead contact on the lead end, wherein said moveable contact is aligned with said lead contact when the lead end is fully inserted into the passageway;
   a rod with a bulge, wherein the connector body has a rod passageway into which the rod is removably insertable; and wherein the rod has a locked position wherein the rod is fully inserted into the rod passageway, wherein said bulge is aligned with said moveable contact, thereby applying a downward force to said moveable contact; and wherein the rod has an open position wherein said bulge is not aligned with said moveable contact, thereby removing the downward force; and
   wherein the lead end may be inserted into the passageway when the downward force on the moveable contact is not present, and wherein the lead end is held in the passageway and a reliable electrical connection is made between the moveable contact and the lead contact when the downward force on the moveable contact is present.

17. The connector system of claim 16 wherein the rod is removable and has an exposed rearward rod end, wherein the rearward rod end protrudes from the connector body when the removable rod is fully inserted into the connector body, and wherein the rearward rod end defines a hook hole, wherein a tool may be attached to the hook hole to remove the removable rod from the connector body.

18. The connector system of claim 16 wherein the removable rod defines a rod latch, and wherein the connector body includes a latch receptacle, and wherein the rod latch and the latch receptacle cooperate to removably retain the removable rod in the rod passageway.

19. The connector system of claim 16 wherein the removable rod has a forward rod end, and wherein the rod latch is on the forward rod end.

20. A connector system comprising;
   a connector body;
   a passageway in the connector body;
   a moveable contact resiliently attached to the connector body;
   a lead end, wherein the lead end is insertable into the passageway;

a lead contact on the lead end, wherein said moveable contact is aligned with said lead contact when the lead end is fully inserted into the passageway;

a captive actuator, wherein the connector body defines an actuator cavity adjacent the passageway, wherein the captive actuator moveably resides within the actuator cavity, wherein the captive actuator may move vertically within the actuator cavity; and a removable key, wherein the connector body defines a key passageway adjacent the actuator cavity and on the side of the actuator cavity opposite the passageway;

wherein the removable key defines a locked position when the removable key is fully inserted into the key passageway; in which locked position the removable key pushes down on the captive actuator, which causes the captive actuator to push down on said moveable contact, thereby applying the downward force to said moveable contact; and wherein the removable key defines an open position when removed from the key passageway, in which open position the captive actuator is not pushed against said moveable contact, thereby removing the downward force; and wherein the lead end may be inserted into the passageway when the downward force on the moveable contact is not present, and wherein the lead end is held in the passageway and a reliable electrical connection is made between the moveable contact and the lead contact when the downward force on the moveable contact is present.

21. The connector system of claim 20 wherein the captive actuator defines a bulge, wherein said bulge is on a surface of the captive actuator facing the moveable contact, and wherein said bulge is aligned with said moveable contact; and wherein insertion of the removable key into the key passageway causes the bulge to push against the moveable contact, thereby applying downward force on the moveable contact.

22. The connector system of claim 20 wherein the removable key has a rearward key end that protrudes from the connector body and a forward key end opposite the rearward key end, and wherein the removable key defines a key bottom surface, wherein the key bottom surface has a downward ramp starting at the forward key end followed by a horizontal surface extending to the rearward key end, and wherein the captive actuator defines an actuator top surface, and wherein the key bottom surface slides over the actuator top surface when the removable key is inserted into the key passageway and placed downward force on the captive actuator.

23. The connector system of claim 20 wherein the removable key has a rearward key end that protrudes from the connector body, wherein the removable key further includes a hook hole at the rearward key end, and wherein a hook may be removably inserted to remove the removable key from the key passageway.

24. The connector system of claim 20 wherein the removable key defines a key latch and the connector body has a latch receptacle, and wherein the key latch and the latch receptacle cooperate to removably retain the removable key in the key passageway.

25. The connector system of claim 20 wherein the removable key has a rearward key end that protrudes from the connector body and a forward key end opposite the rearward key end, wherein the key latch is on the forward key end.

26. A connector system comprising:

a connector body;

a passageway in the connector body;

a moveable contact resiliently attached to the connector body;

a lead end, wherein the lead end is insertable into the passageway;

a lead contact on the lead end, wherein said moveable contact is aligned with said lead contact when the lead end is fully inserted into the passageway; and an actuator, wherein the connector body defines an actuator guide adjacent the passageway, and wherein said actuator moveably reside in said actuator guide, and wherein said actuator is vertically aligned with said moveable contact; and a removable key, wherein the connector body defines a key passageway adjacent the actuator guide, and wherein the removable key is removably insertable into the key passageway;

wherein the removable key defines a locked position wherein the removable key is fully inserted into the key passageway, which insertion causes the removable key to push against said actuator, thereby causing said actuator to exert a downward force against said moveable contact;

wherein the removable key defines an open position wherein removable key is removed from the key passageway, in which open position said actuator does not push against said moveable contact; and wherein the lead end may be inserted into the passageway when the downward force on the moveable contact is not present, and wherein the lead end is held in the passageway and a reliable electrical connection is made between the moveable contact and the lead contact when the downward force on the moveable contact is present.

27. The connector system of claim 26 wherein the removable key has a rearward key end that protrudes from the connector body, and a forward key end opposite the rearward key end, and wherein the removable key further includes a bottom key surface, wherein the bottom key surface includes a downward ramp starting at the forward key end followed by a horizontal surface extending to the rearward end; and wherein the captive actuator has an actuator top surface, and wherein the bottom key surface slides over said actuator top surface when the removable key is inserted into the key passageway, thereby pushing against said actuator and causing said actuator push against the moveable contact.

28. The connector system of claim 26 wherein the removable key has a rearward key end that protrudes from the connector body, wherein the rearward key end defines a hook hole in which a hook may be removably inserted to remove the removable key from the key passageway.

29. The connector system of claim 26 wherein the removable key defines a key latch, and the connector body defines a latch receptacle, wherein the key latch and the latch receptacle cooperate to removably retain the removable key in the key passageway.

30. The connector system of claim 29 wherein the removable key has a rearward key end that protrudes from the connector body, and a forward key end opposite the rearward key end, wherein the forward key end defines the key latch.

31. A connector system comprising;
a connector body;
a passageway in the connector body;
a moveable contact wherein the connector body defines a contact guide adjacent the passageway, and wherein said moveable contact reside in said contact guide;
a lead end, wherein the lead end is insertable into the passageway;
a lead contact on the lead end, wherein said lead contact is aligned with said moveable contact when the lead end is fully inserted into the passageway; and
a removable key, wherein the connector body defines a key passageway adjacent the contact guide, wherein the removable key is removably insertable into the key passageway; and
wherein the removable key defines a locked position, wherein the removable key is fully inserted into the key passageway, which insertion causes the removable key to push against said moveable contact, thereby exerting a downward force against said moveable contact;
wherein the removable key defines an open position, wherein the removable key is removed from the key passageway, thereby relieving the downward force against said moveable contact; and
wherein the lead end may be inserted into the passageway when the downward force on the moveable contact is not present, and wherein the lead end is held in the passageway and a reliable electrical connection is made between the moveable contact and the lead contact when the downward force on the moveable contact is present.

32. The connector system of claim 31 wherein the removable key has a rearward key end that protrudes from the connector body, and a forward key end opposite the rearward key end, and wherein the removable key further has a bottom key surface, wherein the bottom key surface includes a downward ramp starting at the forward key end followed by a horizontal surface extending to the rearward end; and
wherein the moveable contact has a contact top surface, and wherein the bottom key surface slides over said contact top surface when the removable key is inserted into the key passageway, thereby exerting the downward force against the moveable contact.

33. The connector system of claim 31 wherein the removable key has a rearward key end that protrudes from the connector body, wherein the rearward key end defines a hook hole in which a hook may be removably inserted to remove the removable key from the key passageway.

34. The connector system of claim 31 wherein the removable key defines a key latch, and the connector body defines a latch receptacle, wherein the key latch and the latch receptacle cooperate to removably retain the removable key in the key passageway.

35. The connector system of claim 34 wherein the removable key has a rearward key end that protrudes from the connector body, and a forward key end opposite the rearward key end, and wherein the forward key end defines the key latch.

36. A method for connecting a lead of an implantable device to a connector of an implantable device comprising the steps of;
implanting a lead, wherein the lead has a lead end, and wherein the lead end includes a plurality of spaced-apart lead contacts;
implanting a connector, wherein the connector has a passageway, and wherein the lead end is insertable into the passageway, and wherein the connector includes a plurality of spaced-apart movable contacts, wherein the connector includes a means for applying a downward force on the movable contacts whereby the moveable contact are pushed against the lead contacts;
removing the downward force thereby allowing the lead end to be inserted into the passageway;
inserting the lead end into the passageway; and
applying the downward force thereby securing the lead end in the passageway, and providing electrical contact between the moveable contacts and the lead contacts.

37. The method of claim 36 wherein implanting a connector including a means for applying a downward force comprises implanting a connector including a means for applying a downward force, and a means for locking, whereby the downward force is sustained.

38. The method of claim 36 wherein implanting a lead comprises implanting an in-line lead.

39. The method of claim 36 wherein the step of removing the downward force comprises rotating a cam to an open position, wherein the cam includes a plurality of lobes, and wherein in the open position each of the plurality of lobes is pointed away from the movable contacts; and
wherein the step of applying the downward force comprises rotating the cam to a closed position, wherein in the closed position each of the plurality of lobes is pointed towards a respective said movable contacts and pushes a said movable contacts against said lead contacts.

40. The method of claim 36 wherein the step of implanting a connector comprises implanting a connector having a rod passageway, and
wherein removing the downward force comprises removing a removable rod from the rod passageway; and
wherein applying the downward force comprises inserting the removable rod fully into the rod passageway:
wherein the removable rod includes a plurality of bulges, and wherein when the removable rod is fully inserted into the rod passageway, said bulges cooperates with the movable contacts to push the movable contacts firmly against the lead contacts.

41. The method of claim 36 wherein the step of implanting a connector comprises implanting a connector having a key passageway; and
wherein removing the downward force comprises removing a removable key from the key passageway; and
wherein applying a downward force comprises inserting the removable key fully into the key passageway;
wherein the connector includes means for applying the downward force when the removable key is fully inserted into the key passageway.

42. The method of claim 41 wherein the step of implanting a connector having a key passageway comprises implanting a connector having a key passageway, an actuator cavity, and a captive actuator, wherein the captive actuator moveably resides in the actuator cavity, and wherein the actuator cavity resides between the passageway and the key passageway, and wherein the moveable actuator includes a plurality of bulges on a bottom surface of the captive actuator, wherein said bulges are aligned with said movable contacts, and
wherein the step of removing a removable key from the key passageway comprises removing a removable key from the key passageway, wherein in the absence of the removable key in the key passageway the captive actuator does not exert the downward force on the movable contacts; and wherein the step of inserting the removable key fully into the key passageway comprises inserting the removable key fully into the key passageway so that the removable key pushes against the captive actuator causing the captive actuator apply the downward force against the movable contacts, thereby pushing the movable contacts against said lead contacts.

43. The method of claim 41 wherein the step of implanting a connector having a key passageway comprises implanting a connector having a key passageway, a plurality actuator guides, and a plurality of multi actuators moveably residing in the actuator guides, and wherein said actuator guides are defined between the passageway and the key passageway, and wherein the multi actuators are aligned with the movable contacts; and wherein the step of removing a removable key from the key passageway comprises removing a removable key from the key passageway, wherein in the absence of the removable key in the key passageway the multi actuators do not exert the downward force on the movable contacts; and wherein the step of inserting the removable key fully into the key passageway comprises inserting the removable key fully into the key passageway whereby the removable key pushes against the multi actuators causing the multi actuators to apply the downward force against the movable contacts, thereby pushing the movable contacts against said lead contacts.

44. The method of claim 41 wherein the step of implanting a connector having a key passageway comprises implanting a connector having a key passageway, and a plurality of contact guides, wherein the moveable contacts moveably residing in the contact guides, and wherein the contact guides are defined between the passageway and the key passageway; and wherein the step of removing a removable key from the key passageway comprises removing a removable key from the key passageway, wherein in the absence of the removable key in the key passageway the downward force is removed from the movable contacts; and wherein the step of inserting the removable key fully into the key passageway comprises inserting the removable key fully into the key passageway whereby the removable key pushes against the movable contacts applying the downward force against the movable contacts, thereby pushing the movable contacts against said lead contacts.

\* \* \* \* \*